United States Patent [19]

Perry

[11] 4,024,766

[45] May 24, 1977

[54] WASTE WATER SAMPLING SYSTEM

[76] Inventor: Jack A. Perry, 920 Mohawk St., Lewiston, N.Y. 14092

[22] Filed: Jan. 19, 1976

[21] Appl. No.: 650,377

[52] U.S. Cl. .............................. 73/422 R; 73/421 B
[51] Int. Cl.² .......................................... G01N 1/14
[58] Field of Search ........ 73/421 B, 422 R, 422 TC

[56] References Cited
UNITED STATES PATENTS

| 3,771,336 | 11/1973 | Thulin | 73/425.4 P |
|---|---|---|---|
| 3,811,324 | 5/1974 | Doncer | 73/421 B |
| 3,901,087 | 8/1975 | Fabritus | 73/421 B |

FOREIGN PATENTS OR APPLICATIONS 1,270,530 4/1972 United Kingdom .............. 73/421 B

*Primary Examiner*—S. Clement Swisher
*Attorney, Agent, or Firm*—Joseph P. Gastel

[57] ABSTRACT

A liquid sampler including a force main sampling chamber, a seal leg having an end portion immersed in liquid in said sampling chamber, a dam in the sampling chamber for maintaining the liquid at a predetermined minimum elevation therein, a draw tube in communication with the seal leg, a pump for supplying either compressed air or vacuum to the draw tube, first control means for causing the pump to supply vacuum to the draw tube only when a sample is to be taken, a side arm in the draw tube for receiving liquid, second control means including non-contact liquid-level sensing means in the draw tube for causing the pump to supply pressure rather than vacuum after the liquid reaches a predetermined level in the draw tube, and circuit means for terminating operation of the sampling cycle in the event a sample is not taken within a predetermined time period after the sampling cycle is initiated.

14 Claims, 12 Drawing Figures

Fig. 1.

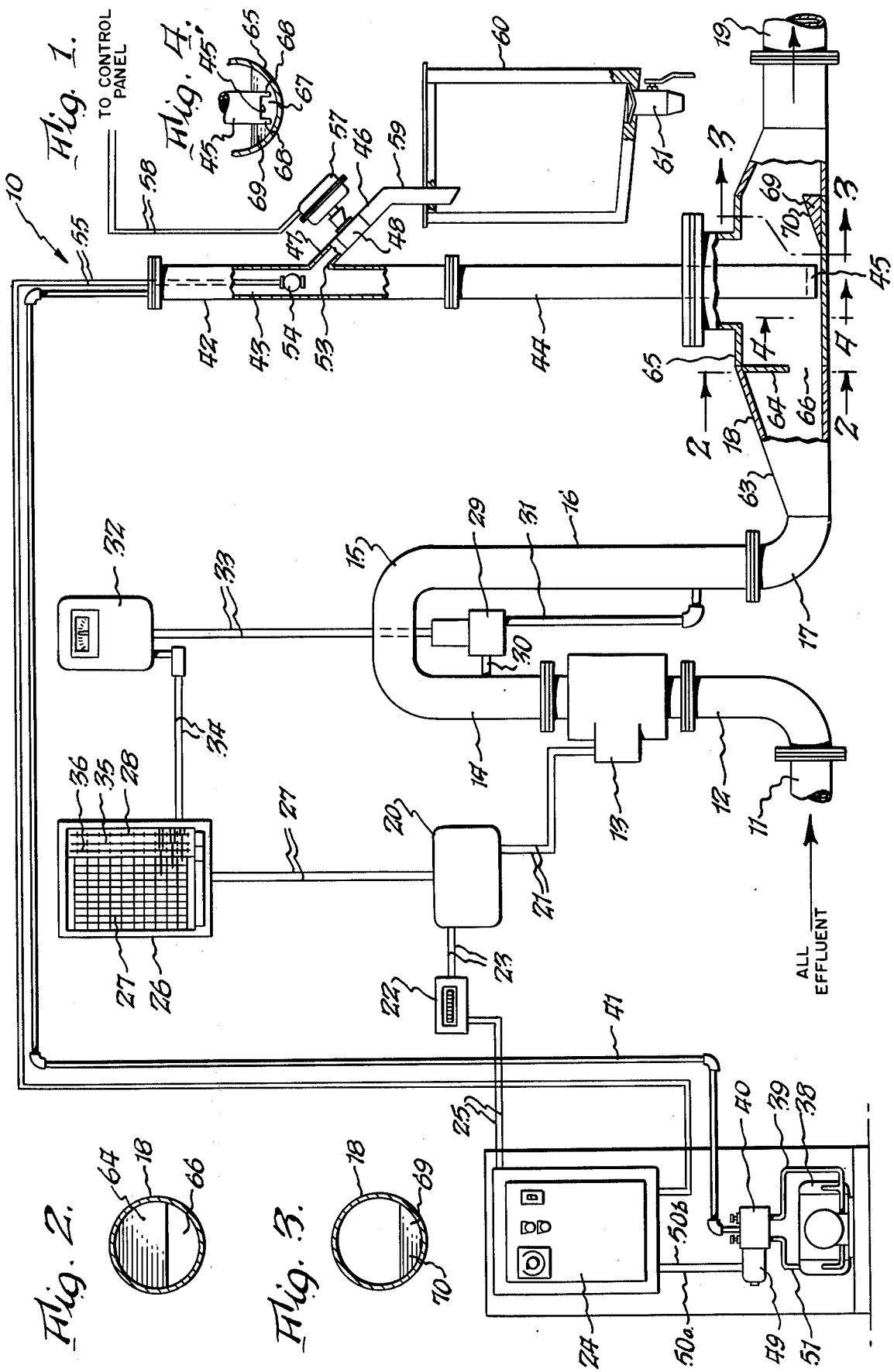

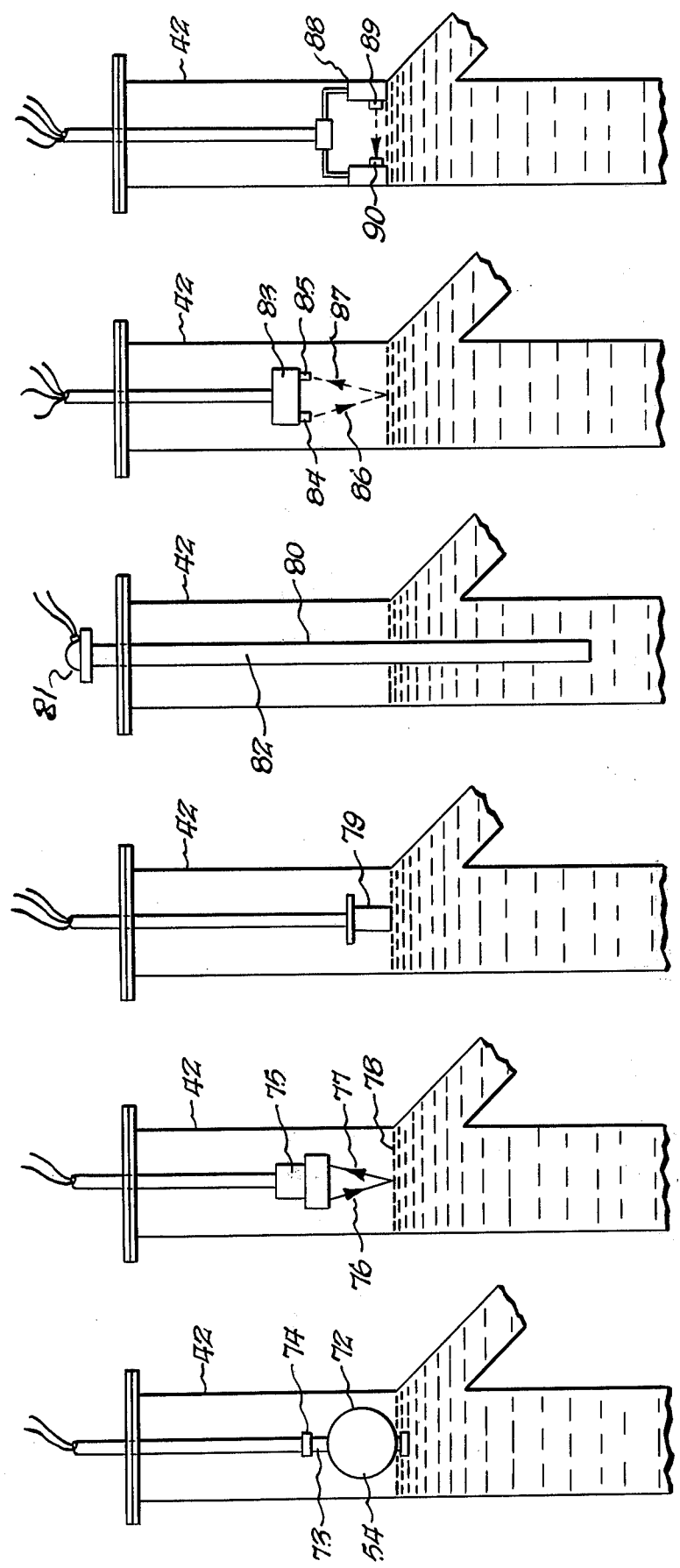

WASTE WATER SAMPLING SYSTEM

The present invention relates to an improved waste water sampling system.

As is well known, governmental regulations require waste water effluent from industrial plants to be monitored. To this end, various systems have been developed. However, it will be appreciated that the effectiveness of the monitoring is greatly dependent on the accuracy and reliability of the monitoring equipment.

It is accordingly one important object of the present invention to provide an improved waste water sampling system which takes precise and representative samples from the effluent. A related object is to provide an improved force main sampling chamber in which the liquid is always maintained above a predetermined level so as to insure that a sample can always be drawn therefrom. A further related object is to provide an improved seal leg construction which tends to cause the waste water flowing past it to be maintained in a state which is representative of all of the waste water flowing through the system. Yet another related object is to provide a flow loop having a meter so oriented therein that it gives an extremely accurate measurement of the amount of flow passing through the system.

Another object of the present invention is to provide a non-contact level sensing device in the sampling tube so that the system will be actuated to perform its function without having any of the electrical contacts thereof actually in contact with the waste water which may foul them.

A further object of the present invention is to provide an improved waste water monitoring system having an improved control circuit which will terminate operation of the sampling cycle in the event a sample is not taken within a predetermined time period after the sampling cycle has been initiated, to thereby permit additional sampling cycles to be initiated. Other objects and attendant advantages of the present invention will be readily perceived hereafter.

The present invention relates to an improved liquid sampler comprising a liquid conduit, a force main sampling chamber in communication with said conduit, a seal leg having an end portion in said sampling chamber, and level maintaining means for maintaining a predetermined level of liquid in said sampling chamber to insure the immersion of said end portion of said seal leg in the liquid in the sampling chamber.

The present invention also relates to an improved liquid sampler comprising a seal leg in communication with a source of liquid to be sampled, a draw tube in communication with said seal leg, a calibrated side arm in communication with said draw tube, pressure supplying means for selectively supplying compressed air or vacuum to said draw tube, and liquid level sensing means above said side arm, said liquid level sensing means including non-contact switch means protected from contact with liquid in said draw tube for causing said pressure supplying means to supply pressure rather than vacuum after the liquid reaches a predetermined level in said draw tube.

The present invention also relates to a liquid sampler system comprising a seal leg, a draw tube in communication with said seal leg, a side arm in communication with said draw tube, a liquid level probe in said draw tube for detecting when the level of liquid therein rises above the level of said side arm, pump means for supplying vacuum or pressure to said draw tube, a dump valve in said side arm, and control circuit means including first circuit means for periodically switching said pump means from pressure to vacuum, second circuit means for shifting said pump means from vacuum to pressure when said liquid level probe detects a predetermined level of liquid, and third circuit means for monitoring said control circuit means to provide a predetermined response in the event of a malfunction therein.

The present invention will be more fully understood when the following portions of the specification are read in conjunction with the accompanying drawings wherein:

FIG. 1 is a view of the improved waste water sampling system of the present invention;

FIG. 2 is a cross sectional view taken substantially along line 2—2 of FIG. 1 and showing the baffle in the force main sampling chamber for directing liquid toward the lower end of the seal leg;

FIG. 3 is a cross sectional view taken substantially along line 3—3 of FIG. 1 and showing the dam in the force main sampling chamber for maintaining a minimum level of liquid;

FIG. 4 is a fragmentary cross sectional view taken substantially along line 4—4 of FIG. 1 and showing the vanes at the lower end of the seal leg for directing liquid flow relative thereto;

FIG. 5 is an enlarged fragmentary schematic side elevational view of the draw leg containing a magnetic float-type level sensing device for switching the system from vacuum to pressure when the liquid reaches a predetermined level;

FIG. 6 is a view similar to FIG. 5 but showing an ultrasonic switch which is actuated by reflected sound waves when the liquid reaches a predetermined level;

FIG. 7 is a view similar to FIG. 5 but showing a temperature responsive switch which is actuated when the liquid level reaches it and the switch senses the different temperature of the liquid;

FIG. 8 is a view similar to FIG. 5 but showing a hydrostatic leg in which the pressure of the air above the liquid increases as the liquid level rises so as to actuate a pressure switch when a predetermined pressure is sensed;

FIG. 9 is a view similar to FIG. 5 but showing a photoelectric cell which actuates a switch in response to sensing a reflected beam from the surface of the liquid when the latter reaches a predetermined level;

FIG. 10 is a view similar to FIG. 5 but showing a switch which is actuated when a photoelectric beam is interrupted when the liquid reaches a predetermined level;

Figure 11:
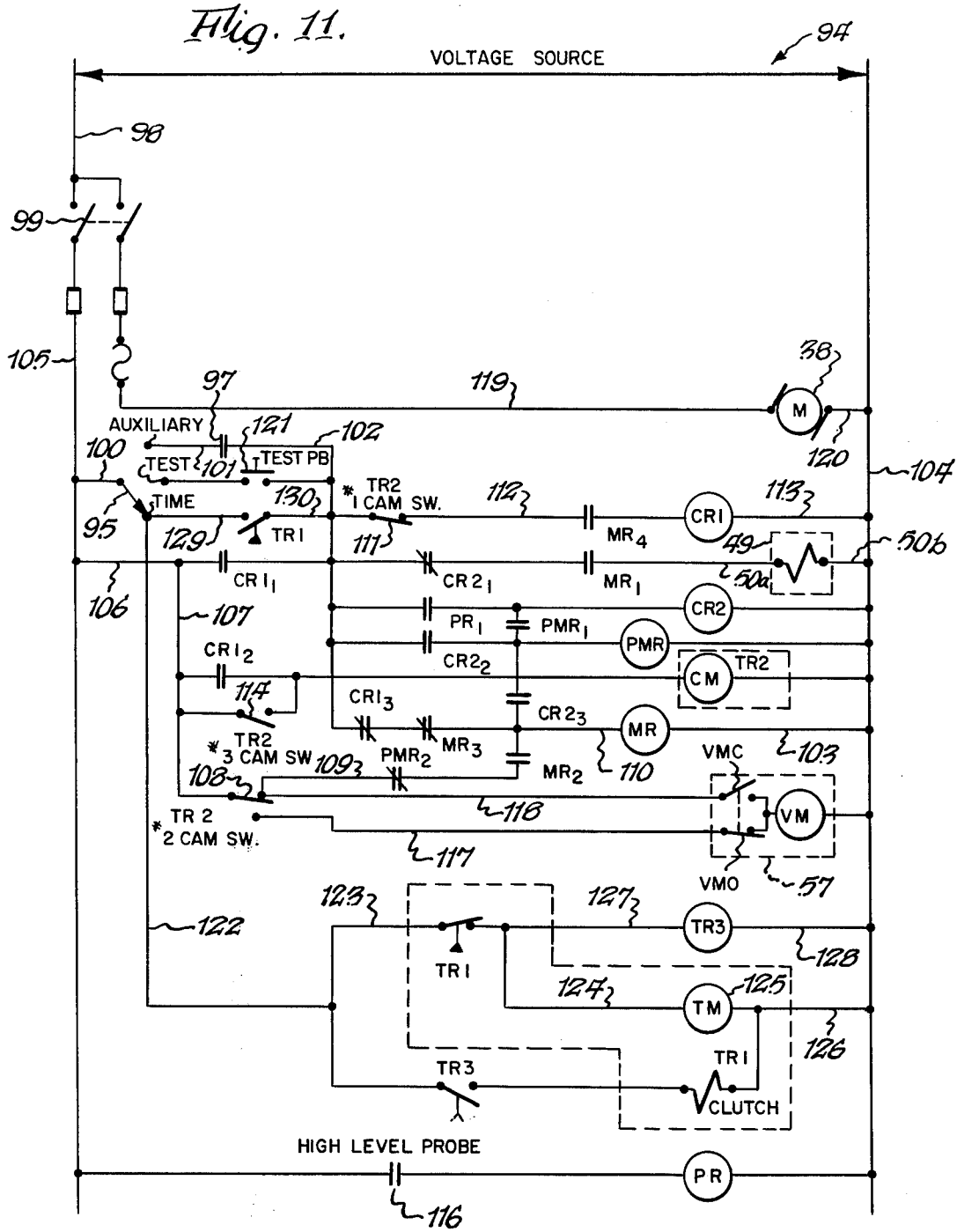
FIG. 11 is a schematic wiring diagram of the electrical circuit used for controlling the sequence of operation and monitoring the circuit.

The waste water sampling system 10 of the present invention includes an effluent inlet conduit 11 which receives all of the effluent which is to be monitored. Conduit 11 is in communication with elbow 12 leading to magnetic flow meter 13 which is positioned in the vertical leg 14 of force main flow metering loop 15 which is of inverted U-shaped configuration. By placing magnetic flow meter 13 in leg 14, its accurate operation is insured because the conduit through flow meter 13 must always have liquid throughout its entire cross section. Vertical leg 16 leading from leg 14 is in communication with elbow 17 which in turn leads to force main sampling chamber 18, which is constructed in such a manner so as to insure accurate and representative sampling of the effluent. Chamber 18 is in communication with conduit 19 leading to the sewer.

As is well understood in the art, various characteristics of the effluent or waste water must be monitored. In this respect, the output of magnetic flow meter 13 is conducted to flow-to-current converter 20 by leads 21. Converter 20 in turn is electrically coupled by leads 23 to flow counter 22 which is coupled to control panel 24 by leads 25. The flow output from converter 20 is also coupled to recorder 26 by leads 27 and the flow will be recorded on chart 27 by a suitable marker and will be read against scale 28 which is suitably calibrated.

A combined unit 29 is provided which receives waste water or effluent through conduit 30 from leg 14 and passes it back to leg 16 through conduit 31. Unit 30 contains the specific ion electrode, the pH electrode and the temperature sensor. A pH transmitter 32 is coupled to unit 29 by leads 33 and the output of pH transmitter 32 is conducted to recorder 26 by leads 34 so that the pH will be recorded on chart 27 and can be read against scale 35. Leads 34 also conduct the temperature data to recorder 26 for recording on chart 27, and the temperature can be read against scale 36. Thus, the flow, pH and temperature are monitored as the effluent passes through the measuring loop 15.

In accordance with required practice, a sample of the liquid flowing through sampling chamber 18 must be taken periodically. The sample may be taken proportionally to effluent flow, and in this respect, counter 22 will provide a signal or pulse each time a predetermined quantity of flow has occurred. The pulse will actuate a control circuit described hereafter. The sampling may also be initiated by momentarily actuating a test push button so that waste water samples may be obtained at any time. The waste water samples may also be obtained on a time basis as a result of a timer periodically actuating the sampling circuit. These modes of operation will be referred to hereafter when the electrical control circuit is described.

When the system is at rest, that is, when a sample is not being taken, a pressure-vacuum pump 38, preferably of the diaphragm type, causes the pressure output thereof to be conducted through conduit 39 to valve 40 which causes pressurized air to be forced into conduit 41 which is in communication with chamber 43 of draw tube 42 which in turn is in communication with conduit or seal leg 44, the lower end 45 of which is immersed in the liquid in chamber 18. Calibrated side arm or conduit 46 has an upper portion 47 in communication with draw tube 43. However, at this time a sample discharge valve 48 is caused to be in a closed position. Therefore, the compressed air will pass through draw tube 22 and seal leg 44 to maintain the latter completely clear of liquid.

Periodically, in response to the actuation of the control circuit, as will be described in greater detail hereafter, valve 40 associated with pressure-vacuum pump 38, will be shifted because of the actuation of motor 49 through leads 50a and 50b to cause vacuum to be communicated to conduit 41 through conduit 51 and valve 40. This will create a vacuum in draw tube 42 and seal leg 44 to cause liquid to rise into draw tube 42 through seal leg 44. The liquid will rise in draw tube 42 until it reaches lip 53 of the calibrated side arm 46 whereupon it will fill the calibrated side arm because the sample discharge valve 48 is closed. After the calibrated side arm portion 47 has been filled, the liquid will continue to rise in chamber 43 until it reaches the level sensor 54 whereupon an electric circuit will be completed through leads 55 to control panel 24. This will cause motor 49 to shift valve 40 to again cause compressed air to be communicated to chamber 43 in draw tube 42 to force the liquid downwardly from the draw tube and seal leg into chamber 18. However, a measured quantity of liquid will be trapped in upper portion 47 of calibrated side arm 46. At a predetermined time thereafter a motor 57 associated with sample discharge valve 48 will be actuated through electrical leads 58 connected to control panel 24 to cause a measured sample to be dumped through conduit 59 into refrigerated compositing chamber 60 which will preserve it in the form in which it was obtained. Periodically valve 61 may be opened to remove the samples from refrigerated chamber 60.

One aspect of the present invention relates to the improved hydraulic arrangement for obtaining accurate representative samples. This aspect is reflected by the use of the inverted U-shaped force main flow measuring loop 15 in which magnetic flow meter 13 is located. This arrangement, as noted briefly above, insures accurate flow measurement because the magnetic flow meter must always see a full cross section of liquid in the conduit associated therewith. Therefore, whenever sampling is based on flow, there is an assurance that sampling is accurate.

The improved hydraulics also includes the force main sampling chamber 18. Essentially this chamber is a conduit having a maximum diameter of 10 inches and it receives its effluent from elbow 17 which is approximately 4 inches in diameter. The significant factor is that the force main sampling chamber 18 is of larger diameter than the inlet conduit thereto and therefore the effluent flow will be slowed down so that the sample can be taken from liquid which is flowing more slowly than it flows in elbow 17 and conduit 16. As can be seen from FIG. 1, the inlet portion 63 of chamber 18 gradually increases in diameter from its relatively small entrance portion of 4 inches to its maximum size of 10 inches. A baffle 64 is located at the junction of inlet portion 63 and uniform diameter portion 65. This baffle forces the flow toward the bottom of chamber 18 through the opening 66, to thereby insure that the flow is directed toward the lower end 45 of seal leg 44.

In accordance with a further aspect of the present invention, the lower portion 45 of the seal leg is cut away at 67 (FIG. 4) so that vanes 68 are formed to provide a path for liquid flow therebetween. This enhances the ease with which liquid is lifted into seal leg 44. This can be more fully understood when it is considered that if the end 45 of the conduit did not have the guiding vanes 68, turbulence could be created as the liquid passed end 45 and such turbulence could conceivably cause the sampling not to be representative of the liquid content because particulate matter might be forced away from the conduit inlet.

Further in accordance with the improved hydraulics, a dam 69 is provided in chamber 18 (FIG. 3). Dam 69 is of the configuration shown and lies across the entire lower portion of the conduit, as can be seen from FIGS. 1 and 3. Dam 69 functions to maintain the level of liquid above the lower end of conduit 45 so that air will not be sucked into seal leg 44 during low flow periods. In other words, regardless of the amount of flow through chamber 18, there must always be a minimum level of liquid therein and this minimum level has to be at least as high as the vertical height of dam 69. Furthermore, the vertical height of dam 69 is above edge 45' of seal leg lower portion 45. The leading edge surface 70 of dam 69 is inclined gradually toward the chamber outlet so that the weir will tend not to accumulate debris and other solid matter.

Another object of the present invention relates to the use of non-contact type of switches for detecting the level of liquid in draw tube 42. Previously switches completed the circuit because of the conductivity provided by the liquid which bridged open contacts. This eventually caused malfunctions in the system because of the accumulation of debris between the open contacts. In accordance with the present invention, any type of non-contact switch, such as shown in FIGS. 5–10, can be used. A non-contact type of switch is one which is actuated without the contacts being engaged by the liquid in tube 42.

One type of non-contact switch which can be used is shown at 54 in FIG. 5. This switch is a magnetic float-reed type of switch which includes a unit 72 containing magnets which can float upwardly on stem 73 until stop 74 is reached. Within stem 73 is a glass envelope housing a reed switch which is opened and closed in response to the movement of the magnets. The glass envelope protects the actual switch contacts from being engaged by the liquid. When the switch contacts close, the pressure cycle will be initiated.

In FIG. 6 another type of non-contact switch is shown which comprises an ultrasonic generator 75 which includes a transmitter for transmitting a sound wave in the direction 76 and for receiving the reflected sound wave which travels in direction 77 when the liquid reaches a predetermined level, and at this time the switch associated with the ultrasonic sensing member will be actuated to initiate the pressure cycle.

In FIG. 7 a temperature responsive switch 79 is shown which completes a circuit to cause pressurized air to be supplied to draw tube 42 when it senses the different temperature of the liquid which contacts it.

In FIG. 8 a hydrostatic leg 80 is shown having a pressure responsive switch 81 associated therewith. When the level of liquid rises to a predetermined height in leg 80, the air trapped above it in chamber 82 will be compressed until switch 81 is closed to actuate the pressure cycle, as described above.

In FIG. 9 a reflected beam type of photoelectric cell 83 is shown which includes a transmitter 84 and a receiver 85. When the liquid reaches a predetermined level in draw tube 42, the transmitted beam 86 will be reflected in path 87 to actuate switch 83 to initiate the pressure cycle.

In FIG. 10 an interrupted beam type of photoelectric cell system 88 is shown in which a transmitter 89 directs a beam at a receiver 90, and this beam is interrupted when the liquid reaches a predetermined level. Upon interruption of the beam, a switch is actuated to provide pressure to draw tube 42 to force liquid therefrom, as described in detail above.

The control circuit 94 (FIG. 11) is initially set up by the selector switch 95 on the auxiliary, test or time contacts, each of which will give a different mode of operation as described hereafter.

Assuming that switch arm 95 is on the auxiliary contact, when a pulse is received at contacts 97 in response to a predetermined flow having been measured by counter 22, a sampling cycle will be initiated. In this respect, a circuit will be completed from line 98 through main switch 99, leads 105 and 100, switch arm 95, the auxiliary contact, lead 101, lead 102, normally closed contacts $CR1_3$ and $MR_3$, monitor relay MR and lead 103 to line 104. The actuation of monitor relay MR will close contacts $MR_1$ and $MR_2$ and $MR_4$ and it will open contacts $MR_3$. However, since $MR_2$ is now closed, a holding circuit will be provided through line 105, leads 106 and 107, closed timer relay No. 2 cam switch 108, lead 109, normally closed contacts $PMR_2$, now closed contacts $MR_2$, lead 110, relay MR and lead 103 to line 104.

The closing of contacts $MR_4$ will energize circuit relay CR1 by completing a circuit from lead 102 to line 104 via closed No. 1 timer relay cam switch 111, lead 112, now closed contacts $MR_4$, circuit relay $CR_1$ and lead 113. The foregoing occurs while the pulse is still across contacts 97. This will cause contacts $CR1_1$ to close to complete a circuit to the switching valve 49 (FIG. 1) between lead 106 and line 104 through now closed contacts $CR1_1$, normally closed contacts $CR2_1$ and now closed contacts $MR_1$, lead 50a and lead 50b. This will energize the vacuum switch 40 to cause the system to change from pressure to vacuum so as to draw a sample into the seal leg 44. At the same time, the closing of contacts $CR1_1$ will provide a holding circuit across relay CR1. Also at this same time, the closing of contacts $CR1_2$ will energize sequence timer CM by completing a circuit from lead 107 to line 104. In addition, the energization of circuit relay CR1 will open the normally closed contacts $CR1_3$, but, as noted above, the monitor relay will remain energized through closed contacts $MR_2$.

The energization of the sequence timer CM will cause three separate switches to be actuated in the proper sequence. No. 3 cam switch 114, which is normally open, will close after two and a half seconds of operation (FIG. 12) to complete a circuit to sequence timer cam motor CM to keep it running to the end of the sequence regardless of what happens to circuit relay CR1. In other words, if circuit relay CR1 should malfunction, it would be immaterial because the circuit is now completed to sequence timer cam motor CM through now closed switch 114 of timer relay TR2.

The sampling system is set up so that the high level probe switch, such as shown in FIGS. 5–10, will be closed before No. 2 cam switch 108 is opened up at 35 seconds if the system is functioning properly. Upon the closing of the contacts 116 at the high level probe switch, such as shown in FIGS. 5–10, relay PR will be energized because of the completion of a circuit across lines 105 and 104 to close the contacts $PR_1$ in line leading to circuit relay CR2 to thereby energize this relay by completing a circuit across lead 102 and line 104. The energization of circuit relay CR2 will open normally closed contacts $CR2_1$ in the line leading to the switching valve 49 and therefore convert the system from vacuum to pressure to purge the draw tube 42 and seal leg 44. Also, the energization of circuit relay CR2 will close normally open contacts $CR2_2$ to complete a circuit across lead 102 and line 104 to the pilot monitoring relay PMR, via lead 106, closed contacts $CR1_1$, lead 102, and now closed contacts $CR2_2$. The energization of relay PMR will close normally open contacts $PMR_1$ to lock in relay CR2 across lines 105 and 104 through now closed contacts $CR2_2$ via lead 106, now closed contacts $CR1_1$, lead 102, now closed contacts CR2₂ and now closed contacts PMR₁. This means that relay CR2 will remain energized regardless of whether high level probe relay PR remains energized. Also, the energization of pilot monitoring relay PMR will open normally closed contacts PMR₂ so that the circuit to monitor relay MR is now through now closed relay contacts CR1₁ and CR2₂ and CR2₃, and no longer through the line in which contacts PMR₂ are located.

Figure 12:
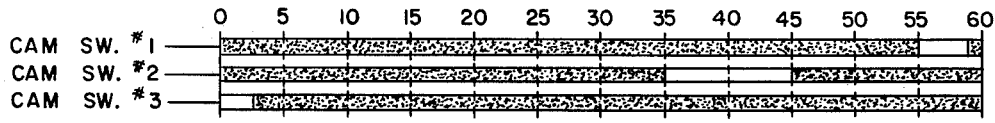
FIG. 12 is a chart showing the operation of the timer cam switches of the electrical circuit.

As can be seen from FIG. 12, at the 35 second mark, No. 2 cam switch 108 will be shifted to complete a circuit through lead 117 and normally closed switch VMO through the sample discharge valve motor 57 across leads 107 and line 104. This will cause valve 48 to be opened and the sample in side arm 46 will be released into the refrigerated compositing chamber 60. The dump valve 48 will remain open for approximately ten seconds and then No. 2 cam switch 108 will shift back to its original position to complete a circuit through the lead 118 and now closed switch VMC to cause the dump valve to close.

The sequence timer cam motor CM will continue to operate until the 55 second mark is reached at which time No. 1 cam switch in lead 112 will open to initiate shutdown of the cycle. In this respect, the circuit to circuit relay CR1 will be terminated which will cause all of the contacts associated with relay CR1 to return to the condition shown in the drawing. This means that contact CR1₃ will return to a closed position, and even though contacts MR3 are in a closed position, monitor relay MR will not be energized because there is no pulse at contacts 97 to initiate the cycle. The opening of contacts CR1₁ is actually what deenergizes the entire system because the main power feed is through this set of contacts. The opening of contacts CR1₂ will have no effect on sequence timer cam motor CM because the feed is now through closed No. 3 cam switch 114 and when No. 3 cam switch 114 runs off to the end, it will open to terminate the flow of current to the cam motor CM.

It is to be noted that pressure-vacuum pump 38 (FIGS. 1 and 11) always remains in operation whenever switch 99 is closed because of the completion of a circuit through motor 38 by leads 119 and 120 which couple motor 38 across lines 98 and 104.

In addition to the above described cycle of operation, which is periodically actuated in response to a pulse produced by counter 22 after a predetermined flow has been experienced, the circuit can be actuated by closing test push button 121 in the event that circuit selector switch 95 is on the test terminal. Whenever test push button switch 121 is closed, the above described cycle of operation will be initiated, considering that the circuit is merely completed by momentarily closing test push button 121 so as to cause the circuit to function in the same manner as if a pulse were applied across contacts 97.

The circuit is also set up to provide sampling at predetermined time intervals. In this event, selector switch 95 is positioned as shown in the drawing so that it is in engagement with the TIME contact. Thus a circuit will be completed from line 105 to line 104 via lead 100, switch 95, lead 122, lead 123, normally closed timer switch TR1, lead 124, timer motor 125, and lead 126. This will cause timer motor 125 to operate. Also, a circuit will be completed through timer relay TR3 through leads 127 and 128 which will cause switch TR3 to close to energize clutch TR1 which will drive switch TR1 which is located between leads 129 and 130.

When switch TR1 between leads 129 and 130 closes, a pulse will be provided to initiate the above-described cycle of operation of the circuit. Continued operation of the timer motor 125 will cause switch TR1 between leads 123 and 127 to open to deenergize relay TR3 to deenergize clutch TR1 and thereafter cause switch TR1 between leads 123 and 127 to close to start the entire timing cycle again. It will be appreciated that any type of timing device or system may be used to momentarily close switch TR1 between leads 129 and 130 to initiate the cycle of operation.

The monitoring system associated with the monitoring relay MR provides a check on whether samples are being taken as required. In this respect, as explained above, the dump valve 48 must open to discharge a sample within 35 seconds because this is built into the system. Thus, the sequence of drawing the sample into the side arm must occur before 35 seconds including the act of causing the water in the draw tube 42 to rise high enough to actuate the switch to switch from vacuum to pressure. If the water does not rise high enough in the draw tube 42 to close the high level probe switch contacts 116 before the 35 second mark is reached which will open No. 2 cam switch 108, the latter will shift over automatically and in so doing will cause the sampling cycle to terminate and the control circuit to be reset to the condition shown in FIG. 11 because the circuit to monitoring relay MR will be terminated because probe relay contacts PR1 will remain open so that there can be no completion of a circuit to maintain monitoring relay MR in operation. The failure to obtain samples as a result of the failure of relay MR to open will occur if the high level probe contacts 116 are not operative or if there is an air leak in either the draw tube 42 or the seal leg 44 or if there is a broken wire in the system or if there is a malfunction of the CR2 relay. In short, the electrical control circuit of FIG. 11 has a monitoring system which will terminate operation of the sampling cycle in the event that a sample has not been drawn properly. When the circuit is reset to the condition shown in FIG. 11 because a sample has not been drawn within 35 seconds, the circuit will be able to again provide a sampling cycle in response to any of the above described modes of initiation. In other words, because of the manner in which the control circuit functions, the circuit will not become "hung-up" in the event a sampling cycle is not completed.

It can thus be seen that the improved waste water sampling system of the present invention is manifestly capable of achieving the above enumerated objects and while preferred embodiments have been disclosed, it will be appreciated that the present invention is not limited thereto but may be otherwise embodied within the scope of the following claims.

What is claimed is:

1. A liquid sampler comprising liquid conduit means, a force main sampling chamber in communication with said conduit means, a seal leg having an end portion in said sampling chamber, level maintaining means for maintaining a predetermined level of liquid in said sampling chamber to insure the immersion of said end portion of said seal leg in said liquid in said sampling chamber, said conduit means being a conduit of a first diameter and said sampling chamber being a conduit of a second diameter which is greater than said first diameter whereby flow in said second conduit is slower than flow in said first conduit, and baffle means extending downwardly from the top of said second conduit and located between said first conduit and said seal leg for defining an opening below said baffle means to insure that flow is directed toward the end portion of said seal leg.

2. A liquid sampler as set forth in claim 1 wherein said level maintaining means comprises a dam in said sampling chamber.

3. A liquid sampler comprising a liquid conduit, a force main sampling chamber in communication with said conduit, a seal leg having an end portion in said sampling chamber, and level-maintaining means for maintaining a predetermined level of liquid in said sampling chamber to insure the immersion of said end portion of said seal leg in the liquid in said sampling chamber, said seal leg being vertical and said end portion of said seal leg including guide vanes for directing flow past said end portion of said seal leg.

4. A liquid sampler as set forth in claim 3 wherein said level maintaining means comprises a dam in said sampling chamber.

5. A liquid sampler as set forth in claim 3 wherein said conduit means is a first conduit of a first diameter and wherein said sampling chamber is a second conduit of a second diameter which is greater than said first diameter whereby flow in said second conduit is slower than flow in said first conduit.

6. A liquid sampler as set forth in claim 6 including baffle means extending downwardly from the top of said second conduit and located between said first conduit and said seal leg for defining an opening below said baffle means to insure that flow is directed toward the end portion of said seal leg.

7. A liquid sampler comprising a liquid conduit, a force main sampling chamber in communication with said conduit, a seal leg having an end portion in said sampling chamber, level-maintaining means for maintaining a predetermined level of liquid in said sampling chamber to insure the immersion of said end portion of said seal leg in the liquid in said sampling chamber, a draw tube in communication with said seal leg, a calibrated normally closed side arm in communication with said draw tube to receive and store liquid obtained from said draw tube when the liquid level in said draw tube tends to rise above the area of communication between said side arm and said draw tube, pump means in communication with said draw tube for selectively providing compressed air and vacuum to said draw tube, and circuit means including non-contact switch means effectively located above the side arm for causing said pump means to switch from vacuum to pressure when the liquid in said draw tube reaches a predetermined level without said liquid actually engaging the contacts of said switch means.

8. A liquid sampler as set forth in claim 7 wherein said seal leg is vertical and wherein said end portion of said seal leg includes guide vanes for directing flow past said end portion of said seal leg.

9. A liquid sampler as set forth in claim 8 wherein said conduit means is a first conduit of a first diameter and wherein said sampling chamber is a second conduit of a second diameter which is greater than said first diameter whereby flow in said second conduit is slower than flow in said first conduit.

10. A liquid sampler as set forth in claim 9 wherein said level maintaining means comprises a dam in said sampling chamber.

11. A liquid sampler comprising a seal leg in communication with a source of liquid to be sampled, a draw tube in communication with said seal leg, a normally closed calibrated side arm in communication with said draw tube to receive and store liquid obtained from said draw tube when the liquid level in said draw tube tends to rise above the area of communication between said side arm and said draw tube, pressure supplying means for selectively supplying compressed air or vacuum to said draw tube, and liquid level sensing means above said side arm, said liquid level sensing means including non-contact switch means protected from contact with liquid in said draw tube for causing said pressure supplying means to supply pressure rather than vacuum after the liquid reaches a predetermined level in said draw tube.

12. A liquid sampler system comprising a seal leg, a draw tube in communication with said seal leg, a side arm having a portion in communication with said draw tube, a liquid level probe in said draw tube for detecting when the level of liquid therein rises above the level of said side arm, pump means for supplying vacuum or pressure to said draw tube, a dump valve in said side arm, and control circuit means including first circuit means for periodically switching said pump means from pressure to vacuum, second circuit means for shifting said pump means from vacuum to pressure when said liquid level probe detects a predetermined level of liquid, third circuit means for opening said dump valve after said side arm has been filled and the liquid in said draw tube has reaches a level below the level of said portion in communication with said side arm, and fourth circuit means for monitoring said control circuit means to provide a predetermined response in the event of a malfunction therein.

13. A liquid sampler system as set forth in claim 12 wherein said predetermined response comprises terminating the sampling cycle and resetting the control circuit means to a condition to perform a subsequent sampling cycle.

14. A liquid sampler system as set forth in claim 13 wherein said fourth circuit means comprises a monitor relay and a cam operated timer switch.

* * * * *

UNITED STATES PATENT OFFICE
CERTIFICATE OF CORRECTION

PATENT NO. : 4,024,766

DATED : May 24, 1977

INVENTOR(S) : Jack A. Perry

It is certified that error appears in the above-identified patent and that said Letters Patent are hereby corrected as shown below:

Column 9, line 27, (claim 6), change "claim 6" to --claim 5--.

Signed and Sealed this second Day of August 1977

[SEAL]

Attest:

RUTH C. MASON
*Attesting Officer*

C. MARSHALL DANN
*Commissioner of Patents and Trademarks*